(12) United States Patent
Verma et al.

(10) Patent No.: US 12,673,128 B2
(45) Date of Patent: ***Jul. 7, 2026

(54) NANO FIBROUS POLYELECTROLYTE COMPLEX FOR RAPID CONTROL OF HEMORRHAGE

(71) Applicant: National Institute of Technology Rourkela, Rourkela Odisha (IN)

(72) Inventors: Devendra Verma, Odisha Rourkela (IN); Sabir Hossain, Burdwan Sadar (IN)

(73) Assignee: NATIONAL INSTITUTE OF TECHNOLOGY ROURKELA, Rourkela Odisha (IN)

( * ) Notice: Subject to any disclaimer, the term of this patent is extended or adjusted under 35 U.S.C. 154(b) by 975 days.

This patent is subject to a terminal disclaimer.

(21) Appl. No.: 17/789,086

(22) PCT Filed: Dec. 31, 2019

(86) PCT No.: PCT/IN2019/050965
§ 371 (c)(1),
(2) Date: Jun. 24, 2022

(87) PCT Pub. No.: WO2021/137246
PCT Pub. Date: Jul. 8, 2021

(65) Prior Publication Data
US 2023/0041921 A1     Feb. 9, 2023

(51) Int. Cl.
*A61L 24/04*     (2006.01)
*A61L 24/00*     (2006.01)

(52) U.S. Cl.
CPC ......... *A61L 24/043* (2013.01); *A61L 24/0042* (2013.01); *A61L 2400/04* (2013.01); *A61L 2400/12* (2013.01)

(58) Field of Classification Search
None
See application file for complete search history.

(56) References Cited

U.S. PATENT DOCUMENTS 12,280,071 B2 * 4/2025 Verma ................ A61K 38/1709

FOREIGN PATENT DOCUMENTS

CN      106480543 B   *  1/2019 ............. B82Y 40/00
KR    20160101374 A   *  8/2016

OTHER PUBLICATIONS

English language translation of KR 2016 0101374 A, Publ. Aug. 25, 2016. (Year: 2016).*
English language translation of CN 106480543 B, Publ. Mar. 8, 2017. (Year: 2017).*

(Continued)

*Primary Examiner* — Dominic Lazaro
(74) *Attorney, Agent, or Firm* — Panitch Schwarze Belisario & Nadel LLP

(57)     ABSTRACT

A polyelectrolyte complex includes nanofibers. The nanofibers include at least one polycationic component and at least one polyanionic component. The nanofibers have a diameter in a range of 20-100 nm. A process for preparing the complex, a method of using the complex, a kit which includes the complex, and a method of inhibiting loss of blood from a wound site by applying the complex to the wound site are also provided.

8 Claims, 5 Drawing Sheets

(56) References Cited

OTHER PUBLICATIONS

Simsek-Ege, et al., Polyelectrolye Complex Formation Between Alginate and Chitosan as a Function of pH, J. Appl. Pol. Sci., 88 (2003) pp. 346-351. (Year: 2003).*

Jeong, S.I., et al., Electrospun Chitosan-Alginate Nanofibers with In Situ Polyelectrolyte Complexation for Use as Tissue Engineering Scaffolds, Tissue. Eng. Part A, 17 (2010) pp. 59-70. (Year: 2010).*

Jeong, S.I., et al., Improved cell infiltration of highly porous 3D nanofibrous scaffolds formed by combined fiber-fiber charge repulsions and ultra-sonication, J. Mater. Chem. B, 2 (2014) pp. 8116-8122 (Year: 2014).*

Int'l Search Report and Written Opinion issued Sep. 21, 2020 in Int'l Application No. PCT/IN2019/050965.

Mendes et al, "Electrostatic self-assembly of polysaccharides into nanofibers," Colloids and Surfaces A: Physiochemical and Engineering Aspects, vol. 531, pp. 182-188 (2017).

Mirzakhanian, et al., Synthesis and characterization of fast-swelling porous superabsorbent hydrogel based on starch as a hemostatic agent, Journal of Biomaterials Science, Polymer Edition, 26:18, pp. 1439-1451 (2015).

Sims, et al., Management of External Hemorrhage in Tactical Combat Casualty Care: The Adjunctive Use of XSTAT™ Compressed Hemostatic Sponges: TCCC Guidelines Change 15-03, J Spec Oper Med., 16(1), pp. 19-28 (2016).

Lewis, et al., Comparison of Two Gelatin and Thrombin Combination Hemostats in a Porcine Liver Abrasion Model, Journal of Investigative Surgery, 26:3, pp. 141-148 (2013).

L'Esperance et al., Controlled survival study of the effects of Tisseel or a combination of FloSeal and Tisseel on major vascular injury and major collecting-system injury during partial nephrectomy in a porcine model; J Endourol., 19 (9), pp. 1114-1121 (2005).

Rong, et al., Alginate-calcium microsphere loaded with thrombin: A new composite biomaterial for hemostatic embolization; International Journal of Biological Macromolecules, 75, pp. 479-488 (2015).

Whang, et al., Hemostatic Agents Derived from Chitin and Chitosan, Journal of Macromolecular Science, Part C: Polymer Reviews, 45, pp. 309-323 (2006).

Devlin, et al., Comparison of ChitoFlex®, CELOX™, and QuikClot® in Control of Hemorrhage; The Journal of Emergency Medicine, vol. 41, Issue 3, pp. 237-245 (2011).

Jaiswal, et al., Hemostatic Efficacy of Nanofibrous Matrix in Rat Liver Injury Model, Surgical Innovation, 24:23-28 (2016).

Delgado, et al., A Novel Biologic Hemostatic Dressing (Fibrin Patch) Reduces Blood Loss and Resuscitation Volume and Improves Survival in Hypothermic, Coagulopathic Swine With Grade V Liver Injury; The Journal of Trauma® Injury, Infection and Critical Care, 64, pp. 75-80 (2008).

Aldridge, et al., Recombinant thrombin approved, Nature Biotechnology, 26(3), pp. 250-250 (2008).

Vyas, et al., Comparison of hemostatic agents used in vascular surgery, Expert Opin Biol Ther., 13(12), pp. 1663-1672 (2013).

* cited by examiner

A                                    B

NANO FIBROUS POLYELECTROLYTE COMPLEX FOR RAPID CONTROL OF HEMORRHAGE

CROSS-REFERENCE TO RELATED APPLICATIONS

This application is a Section 371 of International Application No. PCT/IN2019/050965, filed Dec. 31, 2019, which was published in the English language on Jul. 8, 2021, under International Publication No. WO 2021/137246 A1, the disclosure of which is incorporated herein by reference in its entirety.

TECHNICAL FIELD

The subject matter described herein, in general, relates to a polymer complex, and particularly, relates to a nanofibrous polyelectrolyte complex for controlling haemorrhage.

BACKGROUND OF INVENTION

Haemorrhage is extravasations of blood due to injury to the external (e.g. skin) or internal (e.g. muscle, bone, intestine, liver, pancreas, lung, heart or other tissue) tissue caused by a variety of etiological factors, such as trauma, gunshots, accidents, ulcer, laceration, deep puncture, stabbing or an intentional incision such as a surgical wound. A rapid loss of blood can cause hypovolemic shock and death of the individual. For example, 80% of army soldiers die within 30 minutes after the injury due to massive blood loss. Similarly, almost half of accidental victims die before reaching the point of treatment due to blood loss.

Currently, haemorrhage is controlled by suturing of blood vessels, thermal quarterisation along with compression. However, these methods require skilled medical personnel and are usually not available at the point-of-accident. A number of haemostatic agents, such as Celox™, Trauma-Dex™, XStat™, Hemcon™, Quickclot™ etc., have consequently been developed using a variety of biomaterials, proteins or enzymes. However, most of these products take at least 90-120 seconds, cause a local rise in temperature and/or foreign body reactions, besides having a high cost of production.

Haemostatic biomaterials can be classified into two groups according to their mechanism of action. The first type is the biomaterials that achieve clotting by rapid absorption of the blood, while the second type engages in active bio interactions with the blood to achieve haemostasis.

Absorptive biomaterials impart partial haemostasis simply by absorption of blood and exudates. Cellulose, oxidized cellulose, oxidized regenerated cellulose, and starch-based bandages belong to this category. Various products based on absorption mechanism have been developed (HaemoCer Plus™, Arista™, PerClot™, and Starsil Haemostatic Powders™). Starch-based fast-swelling porous superabsorbent hydrogel (FSPSH) has also been reported (J Biomater Sci Polym Ed. 2015; 26:1439-1451). X-Stat™ by RevMedx is based on the absorptive mechanism (J Spec Oper Med. 2016; 16:19-28). It has been developed for deep wounds, such as gun-shot wounds. However, as it is based on wood pulp, it may cause severe foreign body reaction if left inside the body.

Although there are several instances that point out to certain polymer complexes as a solution for haemorrhagic bleeding, however, there still exists a gap in providing an effective solution for haemorrhagic bleeding in light of existing problems.

SUMMARY OF THE INVENTION

In an aspect of the present disclosure, there is provided a polyelectrolyte complex comprising nanofibers, said nanofibers comprising at least one polycationic component and at least one polyanionic component, wherein the nanofibers have a diameter in a range of 20-100 nm.

In a second aspect of the present disclosure, there is provided a process for preparing the polyelectrolyte complex comprising nanofibers, said nanofibers comprising at least one polycationic component and at least one polyanionic component, wherein the nanofibers have a diameter in a range of 20-100 nm, said process comprising: (a) obtaining a solution-I comprising at least one polycationic component having a pH in a range of 3-5; and (b) obtaining a solution-II comprising at least one polyanionic component having a pH in a range of 6-8; (c) mixing the solution-I and the solution-II, to obtain a mixture; and (d) processing the mixture to obtain the polyelectrolyte complex.

In a third aspect of the present disclosure, there is provided a kit comprising the polyelectrolyte complex, said polyelectrolyte complex comprising nanofibers, said nanofibers comprising at least one polycationic component and at least one polyanionic component, wherein the nanofibers have a diameter in a range of 20-100 nm.

In a fourth aspect of the present disclosure, there is provided a method of inhibiting loss of blood from a wound site, said method comprising: (a) obtaining the polyelectrolyte complex comprising nanofibers, said nanofibers comprising at least one polycationic component and at least one polyanionic component, wherein the nanofibers have a diameter in a range of 20-100 nm; and (b) applying the polyelectrolyte complex to a wound site, for inhibiting blood loss from a wound site.

In a fifth aspect of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the complex is used to inhibit loss of blood from a wound site.

These and other features, aspects, and advantages of the present subject matter will be better understood with reference to the following description and appended claims. This summary is provided to introduce a selection of concepts in a simplified form. This summary is not intended to identify key features or essential features of the claimed subject matter, nor is it intended to be used to limit the scope of the claimed subject matter.

BRIEF DESCRIPTION OF THE DRAWINGS

The detailed description is described with reference to the accompanying figures. The same numbers are used throughout the drawings to reference like features and components.

DETAILED DESCRIPTION OF THE INVENTION

Figure 1:
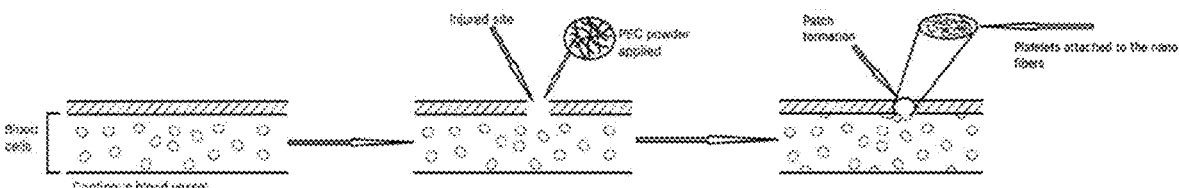
FIG. 1 depicts the clotting mechanism action of the nanofibrous polyelectrolyte complex aggregates, in accordance with an implementation of the present disclosure.

Those skilled in the art will be aware that the present disclosure is subject to variations and modifications other than those specifically described. It is to be understood that the present disclosure includes all such variations and modifications. The disclosure also includes all such steps, features, compositions, and compounds referred to or indicated in this specification, individually or collectively, and any and all combinations of any or more of such steps or features.

For convenience, before further description of the present disclosure, certain terms employed in the specification, and examples are delineated here. These definitions should be read in the light of the remainder of the disclosure and understood as by a person of skill in the art. The terms used herein have the meanings recognized and known to those of skill in the art, however, for convenience and completeness, particular terms and their meanings are set forth below.

The articles 'a', 'an' and 'the' are used to refer to one or more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise" and variations such as "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

Ratios, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a diameter range of 20-100, should be construed to include 30 and 76, and also include sub-ranges such as 35-93, 21-64, 35-90 and so on.

The term "at least one" is used to mean one or more and thus includes individual components as well as mixtures/combinations.

For the purposes of the present disclosure, the term "at least one solvent" includes one or more solvent or mixtures of solvent.

The term "nanofibers" depicts the fibers with a diameter in the nanometer range.

The term "polyelectrolyte complex" or "PEC" depicts the complex formed between two polymers, in which at least one polymer is polycationic and one polymer is polyanionic.

The term "wound site" or "wound" depicts any site on a body of any animal or human that is wounded or has undergone a physical trauma leading to loss of blood. The present disclosure intends to cover the application of the PEC as described herein on the wound site of any animal or human or any living organism which requires any sort of intervention in order to stop the blood loss.

The term "hemocompatible" depicts the compatibility to the red blood cells or blood with any substrate or in the present case with the PEC.

The terms "antimicrobial agent, growth factor, anti-inflammatory agent, anti-histamine, a compound containing copper or silver ions" are used to depict well-known components of the broad category known to a person skilled in the art.

For the purposes of the present disclosure, the term "biomaterial" is intended to depict a material which has the advantage of the material that occurs in nature. The exemplification of the present disclosure has been done using materials that are commercially procured.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the disclosure, the preferred methods, and materials are now described. All publications mentioned herein are incorporated herein by reference.

The present disclosure is not to be limited in scope by the specific embodiments described herein, which are intended for the purposes of exemplification only. Functionally-equivalent products, compositions, and methods are clearly within the scope of the disclosure, as described herein.

The literature is replete with the research work trying to address the problem of haemostasis. However, none of them addresses the problem which the present disclosure has aimed at. Since fibrin plays a crucial role in the formation of a stable clot, fibrin, fibrinogen, and thrombin have been used for haemostatic effect. Fibrin based dressings have shown superior haemostatic performance compared to absorptive dressings (J Trauma Inj Infect Crit Care. 2008; 64:75-80). Products like TachoComb™ and TachoSil™ are some examples of fibrin-based haemostatic agents. In recent years, efforts have also been made to develop recombinant versions of such coagulation proteins (Clin Ther. 2009; 31:32-41). There is only one such example which is clinically approved—Recothrom™, which is a fully recombinant human thrombin (Nat Biotechnol. 2008; 26:250-250). Fibrin dressings have great potential for reducing mortality. However, they are limited by cost, availability, and disease transmission. Fibrin sourced from an animal (bovine, porcine) or human pooled blood pose an additional risk of immunogenicity and viral contamination. Since the reconstitution is required before application, these bandages cannot be used in case of an emergency.

Findings on the role of collagen on coagulation factor localization and activation have inspired collagen-based topical haemostatic products such as Avitene™, Helistat™, Instat, etc. (Expert Opin Biol Ther. 2013; 13:1663-1672). As with animal-sourced fibrin, collagen can also pose immunogenic risks, and therefore to reduce immunogenicity and infectivity, the research has led to the development of gelatin (denatured collagen) based haemostatic agents. Gelatin in both spongy and powder form has been evaluated for haemostatic dressings in surgical procedures (J Investig Surg. 2013; 26:141-148). However, it has shown limited efficacy in controlling severe bleeding. Gelatin has also been evaluated as a liquid haemostatic sealant, e.g., in products like FloSeal where it is combined with thrombin to form injectable haemostatic agent (J Endourol. 2005; 19:1114-1121). These haemostatic agents are composed of macroscopic gelatin particles crosslinked by glutaraldehyde and mixed with bovine thrombin. Since glutaraldehyde is toxic, it may cause an adverse effect if not completely removed.

Alginate and the chitosan are two major bioactive polysaccharides used as haemostatic agents. Alginate microspheres loaded with the antifibrinolytic agent tranexamic acid or the pro-coagulant agent thrombin, have shown promising haemostatic capabilities in vitro and in vivo in preclinical models (Int J Biol Macromol. 2015; 75:479-488). The haemostatic ability of chitosan is thought to originate from its electrostatic interaction with negatively charged cell membranes of RBCs, resulting in RBC agglomeration and thus plug formation (J Macromol Sci Part C Polym Rev. 2005; 45:309-323). Chitosan has also been reported to promote adhesion, activation, and aggregation of platelets. There are many chitosan-based commercially available haemostatic agents, i.e. HemCon™, Celox, Chitoflex™, ChitoGauze™, etc. (J Emerg Med. 2011; 41:237-245).

The most successful zeolite-based material is Quikclot. This material is thought to promote rapid haemostasis via a combination of superabsorbent, platelet activation, and coagulation factor activation capability. However, Quikclot is substantially exothermic and results in local tissue damage. To mitigate tissue damage, Quikclot was used to modify the matrix of standard gauze, resulting in a technology named Quikclot combat gauze (QCG). Another mineral-based technology is WoundStat which uses a smectite mineral and superabsorbent polymers. WoundStat has shown highly efficient haemostasis ability in case of the arterial bleeding. However, further safety studies on the WoundStat have shown several systemic side effects, including vascular endothelial injury, transmural damage, systemic thrombotic, and embolic risks, due to microscopic residues of the material remaining in the wound and blood vessels.

Nanofibrous matrix has also been developed for hemorrhage control. Gelatin and polycaprolactone-based nanofibrous mat originally developed for bone tissue regeneration using electrospinning were found to be highly effective in clotting blood too (haemostasis was achieved within 10 to 15 seconds) (Surg Innov. 2017; 24:23-28). Although, self-assembling peptides are highly biocompatible and show an excellent haemostatic property, the relatively higher cost of these peptides may limit their commercial viability.

The present disclosure discloses a nanofibrous polyelectrolyte complex which can cause rapid clotting of blood to prevent haemorrhage in cases such as, gunshots, accidental trauma, etc., wherein rapid loss of blood occurs as well as for general medical cases such as surgical wounds, lacerations etc. The present disclosure discloses a polyelectrolyte complex as nano-fibrous aggregates of less than 100 nanometer diameter, which can cause rapid clotting of blood in less than 20 sec for massive bleeding and almost instantaneous stoppage of bleeding in surface lacerations, aberration, incision, etc. The disclosure also discloses the process of making such nano-fibrous polyelectrolyte complex through a self-assembly process, which can be carried out at room temperature using specific proportions of a polycationic biomaterial such as, chitosan and a polyanionic biomaterial such as, alginate and washed with tert-butanol to replace the water with alcohol and quick drying over hot surface.

The disclosed nano-fibrous polyelectrolyte complex can be prepared by dissolving stock solutions of polycationic biomaterials, such as chitosan and its derivatives, and polyanionic biomaterials, such as hyaluronic acid, alginate, dextran sulfate, carrageenan, chondroitin sulfate, pectin, polygalacturonic acid, xanthan gum, heparin or their sodium or potassium or calcium salts at room temperature (e.g. 20-25° C.). Both the polycationic and polyanionic biomaterials can be mixed together in the desired weight ratio. The mixture can be washed with low-surface tension organic solvents, such as methanol, ethanol, tert-butanol, acetone or hexane to replace water. The organic solvent can be evaporated by quick drying over a hot surface to produce nano-fibrous polycationic complex having a diameter of less than 100 nanometer.

The polycationic and polyanionic biomaterials ratio ranges from 80:20 to 20:80. Polycationic biomaterials such as chitosan or their derivatives may be obtained prepared in the laboratory by standard protocol or can be obtained from a variety of commercial sources including but not limited to sources, such as Sigma-Aldrich (MO, USA), Hi-Media (Mumbai, India) and Loba Chemie (Mumbai, India). Chitosan or their derivatives may be employed as polycation, for example, derivatives in which acetylation percentage is altered or the polymer length is reduced for the purpose of altering the solubility or other physicochemical properties. Natural polyanions, such as hyaluronic acid, alginate, dextran sulfate, carrageenan, chondroitin sulfate, pectin, polygalacturonic acid, xanthan gum, heparin or their sodium or potassium or calcium salts can be used. The nano-fibrous polyelectrolyte complex may additionally be added with antimicrobials agents, growth factors, debriding agents, etc., to develop would dressing material with haemostatic property. However, the specific embodiments revealed herein are actually the preferred embodiments of the current invention. These features are indispensable or essential.

The nanofibrous polyelectrolyte complex involves the preparation of nano-fibrous polyelectrolyte complex aggregates which has a diameter of less than 100 nanometer and having the ability to quickly clot the blood in less than 20 secs in case of massive damages and almost instantaneously in cases, such as laceration or aberration. In cases of major trauma, such as gunshots, knife stabbing, accidental trauma, automobile accidents, etc., the complex as disclosed herein provides a window of opportunity for the victims to reach the point of treatment without losing much blood. The use of such haemostatic product as disclosed in the present disclosure would be very significant in case of gunshots, stabbing or similar types of injuries which causes severe bleeding.

The disclosed nano-fibrous complex is biocompatible, biodegradable and, when applied to the bleeding surface (e.g. wound), absorbs a substantial amount of fluid and causes blood clotting without undue desiccating the wound site. The polyelectrolytes are macromolecules which exhibit a net positive or negative charge when dissolved in a polar solvent like water. When oppositely charged polyelectrolytes come into contact with each other, they form polyelectrolyte complex or otherwise known as polysalts. The driving force for the formation of a polyelectrolyte complex is the entropy and strong electrostatic attraction between the oppositely charged polymers. When the negatively charged group comes into proximity with the positively charged group, they start attracting each other and an ionically cross-linked material is formed. Crosslink refers to the bonds that link one polymer chain to another polymer. In the presence of some cross-linking agents, the negative functional groups from the same or different chains are attracted to the positive charged functional groups. This cross-linking phenomenon also depends on pH. For example, in the present disclosure, the nano-fibres can only be formed if the pH of the complex is maintained between 4 and 7. Beyond pH values of 7, fibre formation becomes less and more particle formation takes place. When this cross-linked compound comes into contact with blood, it compels the blood cells to get bind or trapped onto the surface of the substrate helping them to create a mesh that leads to a strong patch formation.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm. In another embodiment, the nanofibers have a diameter in a range of 30-90 nm. In yet another embodiment, the nanofibers have a diameter in a range of 40-80 nm. In an alternate embodiment, the nanofibers have a diameter in a range of 40-70 nm.

In an embodiment of the present disclosure there is provided a polyelectrolyte complex comprising nanofibers, said nanofibers comprising at least one polycationic component and at least one polyanionic component, wherein the nanofibers have a diameter in a range of 20-100 nm, and wherein the at least one polycationic component is selected from a group consisting of chitosan or its derivatives, and poly-L-lysine, and combinations thereof. In another embodiment, the at least one polycationic component is selected from a group consisting of chitosan or its derivatives.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the at least one polyanionic component is selected from a group consisting of alginate, hyaluronic acid, dextran sulfate, carrageenan, chondroitin sulfate, pectin, polygalacturonic acid, xanthan gum, heparin, salts thereof, and combinations thereof. In another embodiment, the at least one polyanionic component is selected from a group consisting of alginate, and salts thereof.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the at least one polycationic component is selected from a group consisting of chitosan or its derivatives, and poly-L-lysine, and combinations thereof, and wherein the at least one polyanionic component is selected from a group consisting of alginate, hyaluronic acid, dextran sulfate, carrageenan, chondroitin sulfate, pectin, polygalacturonic acid, xanthan gum, heparin, salts thereof, and combinations thereof.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the at least one polyanionic component and the at least one polycationic component has a weight ratio in a range of 80:20 to 20:80. In another embodiment of the present disclosure, the at least one polyanionic component and the at least one polycationic component has a weight ratio in a range of 70:30 to 30:70. In yet another embodiment, the at least one polyanionic component and the at least one polycationic component has a weight ratio in a range of 60:40 to 40:60. In an alternate embodiment, the at least one polyanionic component and the at least one polycationic component has a weight ratio in a range of 55:45 to 45:55. In one another embodiment, the at least one polyanionic component and the at least one polycationic component has a weight ratio in a range of 53:47 to 47:53.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the at least one polycationic component is selected from a group consisting of chitosan or its derivatives, and poly-L-lysine, and combinations thereof, and wherein the at least one polyanionic component is selected from a group consisting of alginate, hyaluronic acid, dextran sulfate, carrageenan, chondroitin sulfate, pectin, polygalacturonic acid, xanthan gum, heparin, salts thereof, and combinations thereof, and wherein the at least one polyanionic component and the at least one polycationic component has a weight ratio in a range of 80:20 to 20:80. In another embodiment, the at least one polyanionic component and the at least one polycationic component has a weight ratio in a range of 70:30 to 30:70.

In an embodiment of the present disclosure, there is provided a process for preparing a polyelectrolyte complex comprising nanofibers, said nanofibers comprising at least one polycationic component and at least one polyanionic component, wherein the nanofibers have a diameter in a range of 20-100 nm, said process comprising: (a) obtaining a solution-I comprising at least one polycationic component having a pH in a range of 3-5; and (b) obtaining a solution-II comprising at least one polyanionic component having a pH in a range of 6-8; (c) mixing the solution-I and the solution-II, to obtain a mixture; and (d) processing the mixture to obtain the polyelectrolyte complex. In another embodiment, the solution-I has a pH in a range of 3.5-6, and the solution-II has a pH in a range of 6.5-7.5.

In an embodiment of the present disclosure, there is provided a process for preparing a polyelectrolyte complex comprising nanofibers as described herein, wherein the mixing of the solution-I and the solution-II is done in a dropwise manner having a rate in a range of 5-15 ml/minute.

Embodiment of the present disclosure, there is provided a process for preparing a polyelectrolyte complex comprising nanofibers as described herein, wherein the mixing of the solution-I and the solution-II is done is done by adding the solution-I in a dropwise manner to the solution-II with a rate in a range of 5-15 ml/minute. In another embodiment, the rate is in a range of 7-12 ml/minute. In yet another embodiment, the rats is 10 ml/minute.

In an embodiment of the present disclosure, there is provided a process as described herein, wherein the processing comprises: (i) sonicating the mixture to obtain a sonicated sample; and (ii) washing the sonicated sample with at least one organic solvent followed by drying the sample, to obtain the polyelectrolyte complex. In another embodiment, the at least one organic solvent is a low surface tension organic solvent. In yet another embodiment, the at least one organic solvent is selected from a group consisting of methanol, ethanol, butanol, acetone, hexane, and combinations thereof.

In an embodiment of the present disclosure, there is provided a process for preparing a polyelectrolyte complex comprising nanofibers, said nanofibers comprising at least one polycationic component and at least one polyanionic component, wherein the nanofibers have a diameter in a range of 20-100 nm, said process comprising: (a) obtaining a solution-I comprising at least one polycationic component having a pH in a range of 3-5; and (b) obtaining a solution-II comprising at least one polyanionic component having a pH in a range of 6-8; (c) mixing the solution-I and the solution-II, to obtain a mixture; and (d) processing the mixture to obtain the polyelectrolyte complex, and wherein the at least one polycationic component is selected from a group consisting of chitosan or its derivatives, and poly-L-lysine, and combinations thereof, and wherein the at least one polyanionic component is selected from a group consisting of alginate, hyaluronic acid, dextran sulfate, carrageenan, chondroitin sulfate, pectin, polygalacturonic acid, xanthan gum, heparin, salts thereof, and combinations thereof, and wherein the at least one polyanionic component and the at least one polycationic component has a weight ratio in a range of 80:20 to 20:80. In another embodiment, the at least one polyanionic component and the at least one polycationic component has a weight ratio in a range of 70:30 to 30:70.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the complex further comprises different type of salts. In another embodiment, the salts like calcium chloride, sodium tri-polyphosphateare used.

In an embodiment of the present disclosure there is provided a polyelectrolyte complex comprising nanofibers, said nanofibers comprising at least one polycationic component and at least one polyanionic component, wherein the nanofibers have a diameter in a range of 20-100 nm, and wherein the complex further comprises at least one compound selected from a group consisting of at least one antimicrobial agent, at least one growth factor, at least one anti-inflammatory agent, at least one anti-histamine, at least one compound containing copper or silver ions, and combinations thereof.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the complex has a pH in a range of 3-7. In another embodiment, the complex has a pH in a range of 4-7.

In an embodiment of the present disclosure, there is provided a polyelectrolyte complex comprising nanofibers, said nanofibers comprising at least one polycationic component and at least one polyanionic component, wherein the nanofibers have a diameter in a range of 20-100 nm, and wherein the complex is hemocompatible, biodegradable and non-cytotoxic.

In an embodiment of the present disclosure, there is provided a polyelectrolyte complex as described herein, wherein the nanofibers is present in at least one form selected from a group consisting of thread, string, mesh, gauze, porous, sponge, and combinations thereof.

In an embodiment of the present disclosure, there is provided a polyelectrolyte complex as described herein, wherein the complex is in at least one form selected from a group consisting of a patch, a bandage, a wound dressing material, and combinations thereof.

In an embodiment of the present disclosure, there is provided a kit comprising the polyelectrolyte complex as described herein. In another embodiment, the kit further comprises an instruction manual for using the complex.

In an embodiment of the present disclosure, there is provided a method of inhibiting loss of blood from a wound site, said method comprising: (a) obtaining the polyelectrolyte complex as described herein; and (b) applying the polyelectrolyte complex to a wound site, for inhibiting blood loss from a wound site. In another embodiment, the loss of blood is inhibited within 50 seconds of applying to the wound site. In yet another embodiment, the loss of blood is inhibited in a range of 5-50 seconds of applying.

In an embodiment of the present disclosure, there is provided a method of inhibiting loss of blood from a wound site, said method comprising: (a) obtaining the polyelectrolyte complex as described herein; and (b) applying the polyelectrolyte complex to a wound site, for inhibiting blood loss from a wound site. In another embodiment, the loss of blood is inhibited within 20 seconds of applying to the wound site. In yet another embodiment, the loss of blood is inhibited in a range of 5-20 seconds of applying.

In an embodiment of the present disclosure, there is provided a polyelectrolyte complex as described herein, wherein the complex is present in at least one form selected from a group consisting of thread, string, mesh, guage, porous material, sponge, and combinations thereof.

In an embodiment of the present disclosure, there is provided a polyelectrolyte complex as described herein, wherein the complex is present in at least one form selected from a group consisting of powder, patch, bandage, wound dressing material, and combinations thereof.

In an embodiment of the present disclosure, there is provided a polyelectrolyte complex as described herein, wherein the complex is in the form of a powder.

In an embodiment of the present disclosure, there is provided a kit comprising the polyelectrolyte complex as described herein in the form of a powder, and an instruction manual for using the powder on a wound.

In an embodiment of the present disclosure, there is provided a polyelectrolyte complex as disclosed herein, wherein the complex can be made in powder form, gel form or in liquid form. Furthermore, the present disclosure is not limited to polyelectrolyte complex only, composed of polysaccharides, moreover as other hemostats such as biological hemostats, bioactive glasses, molecular sieve materials, thrombin, fibrin, other similar materials or combinations of the aforesaid with the present embodiment are within the scope of the current disclosure. Some clay or other clotting materials of some embodiments can also be mixed with the present embodiment or may be used in conjugation, to improve the efficacy of the polyelectrolyte complex of the present disclosure. Some of the embodiments may include, mixing or incorporating various materials into the present disclosure to maintain or improve the antiseptic environment at the trauma site. For example, antibiotics, anti-fungal agents, anti-inflammatory agents, anti-microbial agents, anti-histamines, compounds containing copper or silver ions, analgesics, and combinations thereof can be used. Biological haemostatic materials such as human serum albumin, bovine thrombin, calcium, human thrombin (hThrombin), rhThrombin, factor XIII, factor VIIa, recombinant Factor XIII (rFactor XIII), prostaglandin-2a, thromboxane A2, epidermal growth factor, tumor necrosis factor (TNF), platelet derived growth factor, TNF-alpha, transforming growth factor (TGF), Von Willebrand factor, TGF-alpha, TGF-beta, fibroblast growth factor, nerve growth factor, insulin like growth factor, keratinocyte growth factor, penicillin, methicillin, ampicillin, amoxycillin, clavulanic acid, clavamox, aztrenam, streptomycin, imipenem, kanamycin, bacitracin, tobramycin, vancomycin, polymyxin, gentamicin, clindamycin, erythromycin, amphotericin, rifampicin, nystatin, tetracycline, doxycycline, chloramphenicol, fibrin, thrombin, ascorbic acid, rutin, tranexamic acid, combination of aforesaid or similar materials can be used with the present embodiment, to provide additional haemostatic functions, depending on the nature of the injury. Also, the plant-derived agents which are having desirable effects at the trauma site can be used with the present embodiment, such as, *Glycyrrhiza glabra, Thymus vulgaris, Alpinia officinarum, Vitis vinifera* and *Urtica dioica, Newbouldia laevis* (Leaves), *Annona senegalensis* (Leaves), *Cissampelos mucronata* (aerial part), *Cassytha fihformis* (aerial part) etc.

In an embodiment of the present disclosure, there is provided a process as described herein, wherein the at least one solvent can also be any other alcohol or similar material that is capable of replacing the water from the suspension of polyelectrolyte complex. The water replacing material may be any other single alcohol, a mixture of more than one alcohol, mixture of water and alcohol or a combination of the aforesaid. After repetitive washing with alcohol, the polyelectrolyte complex and alcohol suspension was dried at 100° C. which gives the nano-fibrous material.

Numerous types of materials and different combinations of materials may be used for the polyelectrolyte of the present disclosure. The fibrous structure may be composed of single or more fibres like thread or string; mesh; gauze; woven or non-woven; absorbent or non-absorbent; tightly woven textile; porous or solid; sponge etc.

The steps of processing the mixture which includes the step of sonicating the mixture to obtain a sonicated sample and washing the sonicated sample followed by drying can be done in different ways. In some embodiments, direct using of spray drier can give the final product. In some embodiments, the process may be accomplished in two steps, first by drying the substrate, and second by transforming the dried substrate into form. For drying the substrate there are several ways: this involves elevation of temperature of the surrounding air of the substrate up to a level which is equal or more than the boiling temperature of the water replacing material. In some embodiments, direct heat can be applied to the substrate itself by any measures. In some embodiments, drying process can comprise vacuum drying, where the drying is performed by creating a constant vacuum to remove the evaporated materials consistently. In some embodiments, drying may include lyophilisation. The drying parameters such as temperature, vacuum level, duration and/or pressure can be varied or adjusted to produce the product. Transferring the dried substrate into the desired form can be done in several ways. In some embodiment it can be done by crushing the material or by grinding the substrate or by any other method which does not significantly deteriorates the haemostatic property of the substrate. In some embodiment both heating and grinding can be done at the same time.

In the present disclosure, the disclosed haemostatic agent has a high absorbency to one or more liquids like water and blood. In some embodiment the substrate may be capable of absorbing at least 4 times or at least 10 times or even more of its initial dry weight.

For the justification of the ability of the polyelectrolyte complex described in the present disclosure, characterization of the polyelectrolyte complex was performed by using FESEM, BET surface area analyser. For ensuring the cell adhesion ability of the substrate in the current embodiment, blood with the substrate was interrogated by using FESEM. Compressive mechanical strength of the clots was also measured using UTM. The current embodiment also includes the ability of the polyelectrolyte complex to withstand the blood pressure at the injury site. It refers that the polyelectrolyte complex will remain there at the injury site after applying and will not flow away with the blood flow and instead of that it will create a strong patch over the injured site so that no further bleeding will happen.

The disclosed nano-fibrous polyelectrolyte complex typically can be placed in suitable sealed packaging (e.g. pouch or a vial made of suitable materials, or a kit containing such packaging and optionally contains printed instructions) and subjected to sterilization before being further packaged if need be with printed instructions describing the proper use of the material or kit in the treatment of haemorrhage. Suitable sterilization methods include ionizing radiation (e.g. gamma radiation) or ethanol treatment.

The disclosed nano-fibrous polyelectrolyte complex may be applied directly (e.g. for clean wounds) or as a part of a multi-step treatment regimen (e.g. for infected wound). The multi-step treatment regimen may include or be followed by a cleaning and disinfection followed by the application of the disclosed nano-fibrous polyelectrolyte complex.

Although the subject matter has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present subject matter as defined.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein. It is to be understood that this disclosure is not limited to particular methods, and experimental conditions described, as such methods and conditions may apply.

The present section exemplifies the present disclosure by means of working and non-working examples. Also, the method of preparation of the nanofibrous complex has been described in detail. FIG. 1 depicts the mechanism of blood clotting using nanofibrous material.

In the present disclosure, two water-soluble materials were mixed together. Polycation, such as chitosan and polyanions, such as alginate were used as the primary components to form the nano-fibrous polyelectrolyte complex. The formation of the complex is spontaneous and accompanied by the release of counterions. The processing is completely aqueous-based and does not require any toxic solvents.

After preparing the polyelectrolyte complex, a water replacing material (methanol, ethanol, butanol, acetone or hexane) was introduced in the very next step of the fabrication process. This water replacing material plays a key role in the fabrication of the dry nano-fibrous polyelectrolyte complex. It helps in keeping nano-fibers from agglomeration as per the present disclosure.

When the water molecules are replaced by the said material (water replacing material) and heated up, the water replacing material evaporates, leaving behind nano-pores and fibrous structure, which in turn increases the surface-to-volume ratio of the nano-fibres. This enhanced surface-to-volume ratio leads to a higher absorption property of the nano-fibrous samples. Herein, the prepared polyelectrolyte complex was washed with low surface tension organic solvents such as, methanol, ethanol, butanol, acetone or hexane to replace the water molecules, which later helps in creating pores and fibrous structure during the drying process. In the present disclosure, tertiary butanol gives the best result and the resulting final fibrous exhibits a nano-structure with a fibre diameter of less than 100 nm.

Polycationic biomaterial including, but not limited to, chitosan and poly-L-Lysine can be used. In the present disclosure, chitosan as a polycationic material gives the best result. Chitin derived, chitosan is a natural biopolymer, a major component of crustacean outer skeletons.

Polyanionic biomaterials including, but not limited to, hyaluronic acid, alginate, dextran sulfate, carrageenan, chondroitin sulfate, pectin, polygalacturonic acid, xanthan gum, heparin or their sodium or potassium or calcium salts can be used. In the present disclosure, sodium alginate as a polyanionic biomaterial gives the best result. Alginate is copolymer with linear structure that consists of two polymeric links, i.e. (1-4)-linked β-D-mannuronic acid (M) and a-L-guluronic acid (G) residues. The two monomeric units are of uronic acids and their relative concentration vary along the polymer chain along with their arrangement, depending on the origin of the alginate.

Example 1

Polyelectrolyte Complex (PEC) Preparation

The PEC as per the present disclosure was prepared by using chitosan which was commercially procured from HiMedia Laboratories (Catalog No. TC242). Chitosan as used was having a degree of deacetylation >75% with molecular weight in a range of 3800-20000 g/mol. Sodium alginate was commercially procured from HiMedia Laboratories (Catalog No. MB114) with average molecular weight of 703161 g/mol. Although the present disclosure has been exemplified by using the components as described above, but it is well understood that the components obtained by any other commercial vendor with slight variations in the molecular weight can also be used.

1 g of chitosan was dissolved in 100 ml of 1% acetic acid solution (solution-I) and 1 g of sodium alginate was dissolved in 100 ml of deionized water (solution-II), respectively. A continuous overnight stirring was required for the complete dissolution of both the polymers. The pH for the chitosan solution was set at 4 and the pH for the sodium alginate solution was set at 7. The chitosan solution was then added dropwise (10 ml/minute) to the sodium alginate solution which forms beads (mixture) in the solution. Three different ratios of mixture ware prepared. The detailed composition of the aforesaid samples is described in Table 1 below. After that, each sample was sonicated for 30 minutes and processed further to get the polyelectrolyte complex. The final pH of the polyelectrolyte complex (PEC) was 4.7.

TABLE 1

| | Compositions of all chitosan/alginate-based polyelectrolyte complex nanofibers | | |
|---|---|---|---|
| S. No. | Sample name | Alginate percentage (%) | Chitosan percentage (%) |
| 1 | AL30CH70 (Sample 1) | 30 | 70 |
| 2 | AL50CH50 (Sample 2) | 50 | 50 |
| 3 | AL70CH30 (Sample 3) | 70 | 30 |
| 4 | AL50CH50 (films) | 50 | 50 |

The sonicated samples were centrifuged at a speed of 5000 rpm for 10 minutes. The sample settled at the bottom and the water was discarded. Then the same amount of tertiary butyl alcohol was added to the sample and was mixed properly by vortexing. The mixture was left as it is for a night. After that, the mixture was centrifuged and the alcohol was discarded. This step was repeated 3 times. Then alcohol was added to the resulting sample and was mixed well by vortexing. An aluminium foil was wrapped on the heating plate of a stirrer and the temperature was set at 100° C. After that, with the help of a syringe the sample plus alcohol mixture was sprayed over the heated aluminium foil to let that dry. The dried polyelectrolyte complex (PEC) was simply taking out from the foil and collected in a falcon tube. The flakes of the PEC were then further made finer by using a vibrator. Replacement of water with alcohol before drying is an important step. If PEC suspension is dried with water replacement, the PEC fibres clump together and turns into film instead of nanofibrous aggregates. AL50CH50 films (AL50CH50_film) were also prepared without the replacement of water with alcohol.

The PEC complex as described herein is intended to cover any composition of PEC in which the ratio of at least one polyanionic component and the at least one polycationic component lies in a range of 80:20 to 20:80. According to one of the implementation, the ratio lies in a range of 70:30 to 30:70. The PEC formed outside the ratio of 80:20 to 20:80 suffers from a problem of wastage of the polycationic component or the polyanionic component after the PEC is formed. For example, the PEC formed from the 85:15 ratio of the polyanionic component to the polycationic component leads to the formation of PEC utilizing an equal amount of chitosan and alginate while rest of the polyanionic component is washed off or wasted. Therefore, the formation of PEC by varying the ratio of polycationic component and polyanionic component outside 80:20 to 20:80 would not be economically significant, since it leads to wastage of either of the component used for the formation of the PEC.

Example 2

Imaging of the PEC Obtained by Using Various Ratios

For the physical characterization of the PEC and to verify whether they have nano-structures or not, FESEM imaging of different samples were performed. In the FESEM imaging, it was found that they have a nano-fibrous structure with a fiber diameter ranging from 20 to 100 nm.

Figure 2:
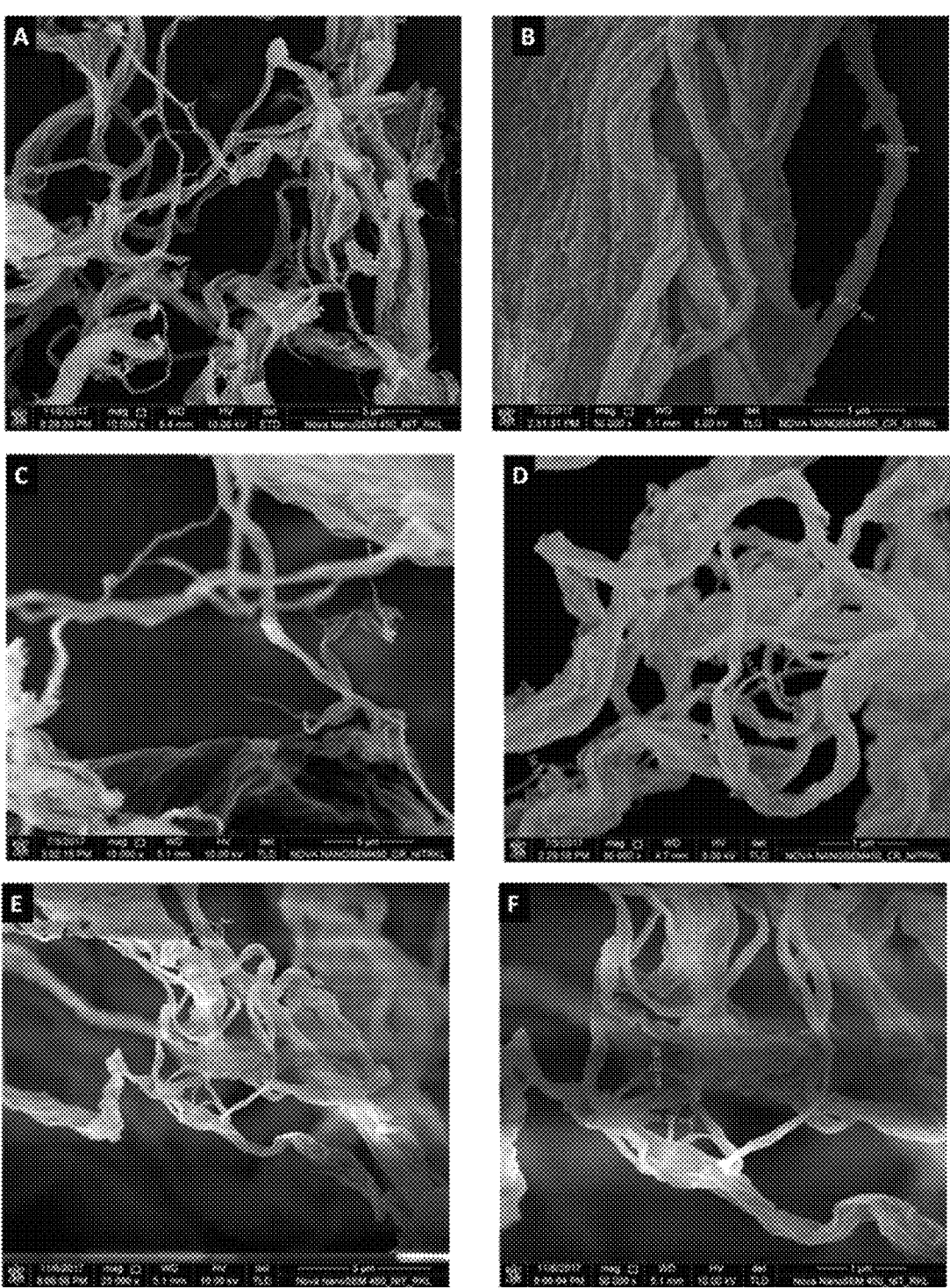
FIG. 2(A-F) depicts Field Emission Scanning Electron Microscope (FESEM) imaging of the polyelectrolyte complex (PEC) samples, in accordance with an implementation of the present disclosure.

FIG. 2 shows the nano-fibrous structure of the PEC. FIGS. 2A and 2B are of AL30CH70 PEC, FIGS. 2C and 2D are of AL50CH50, and FIGS. 2E and 2F are of AL70CH30 respectively. From FIG. 2A-2F, it can be observed that the diameter of the fibres is in a range of 20-100 nm which is desired as per the PEC of the present disclosure.

It can be appreciated that the three PEC samples prepared as per the method described in Example 1 have nanofibrous structures as desired.

Example 3

Whole Blood Clotting Assay

In this test, 2004, of blood was taken into an Eppendorf tube, and to that 20 µL of 0.2 M calcium chloride solution and PEC, was added simultaneously. This procedure was repeated for each of the samples. Clotting of the blood was ensured by shaking the Eppendorf tube to see whether the blood has any movement or not. Also, the time was noted. For comparison with the PEC of the present disclosure, Celox™ was taken as a reference. Respective clotting times of different samples are mentioned in Table 2.

TABLE 2

Whole blood clotting time of PEC samples.

| Sample No. | Samples | Blood Clotting time (Seconds) |
|---|---|---|
| 1 | AL30CH70 | 34 ± 2 |
| 2 | AL50CH50 | 15 ± 3 |
| 3 | AL70CH30 | 25 ± 3 |
| 4 | AL50CH50 Film | 214 ± 2 |
| 5 | Pure Blood | 282 ± 14 |
| 6 | Celox ™ (30%) | 98 ± 6 |

All the nanofibrous PEC samples exhibited significantly lower clotting time compared to controls and AL50CH50_Film. AL50CH50 exhibited the lowest clotting time of 15±3 seconds among the nanofibrous PECs. AL50CH50_film exhibited clotting time of 214±2 seconds, which suggests that nanofibrous structure plays a critical role in the clotting of the blood since the film has a thickness of around 100 microns.

Example 4

Cell Adhesion Test

Figure 3:
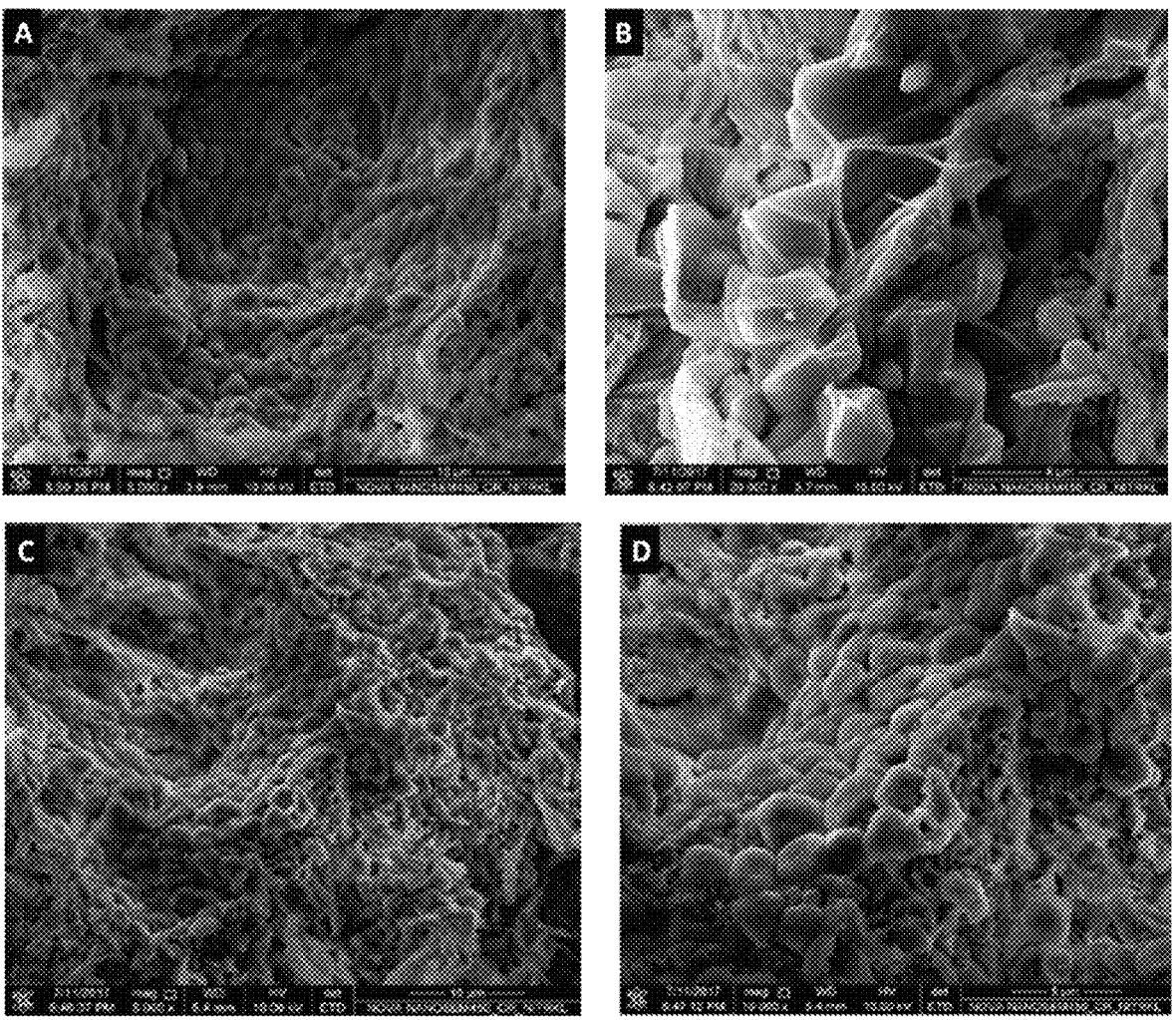
FIG. 3(A-D) depicts FESEM images of the blood clots treated with different PEC samples, in accordance with an implementation of the present disclosure.

AL70CH30 and AL50CH50, that were prepared through the procedure of example, were used to clot blood samples. After the whole blood samples were clotted, the clot samples were fixed by dipping them in formalin for 12 hrs. After that, the fixed clots were taken out and dipped into tertiary bully alcohol for 12 hrs. Then the samples were dried in a vacuum drier. Clot samples were then brought for FESEM imaging. FIG. 3 shows the FESEM imaging test results. FE-SEM images indicate that cells are adhering on both formulations irrespective of their difference in compositions. FE-SEM images of blood clots, treated with AL70CH30 PEC powder (A, B) and AL50CH50 (C, D) at lower and higher magnification respectively.

Example 5

Compressive Mechanical Strength Measurement

Figure 4:
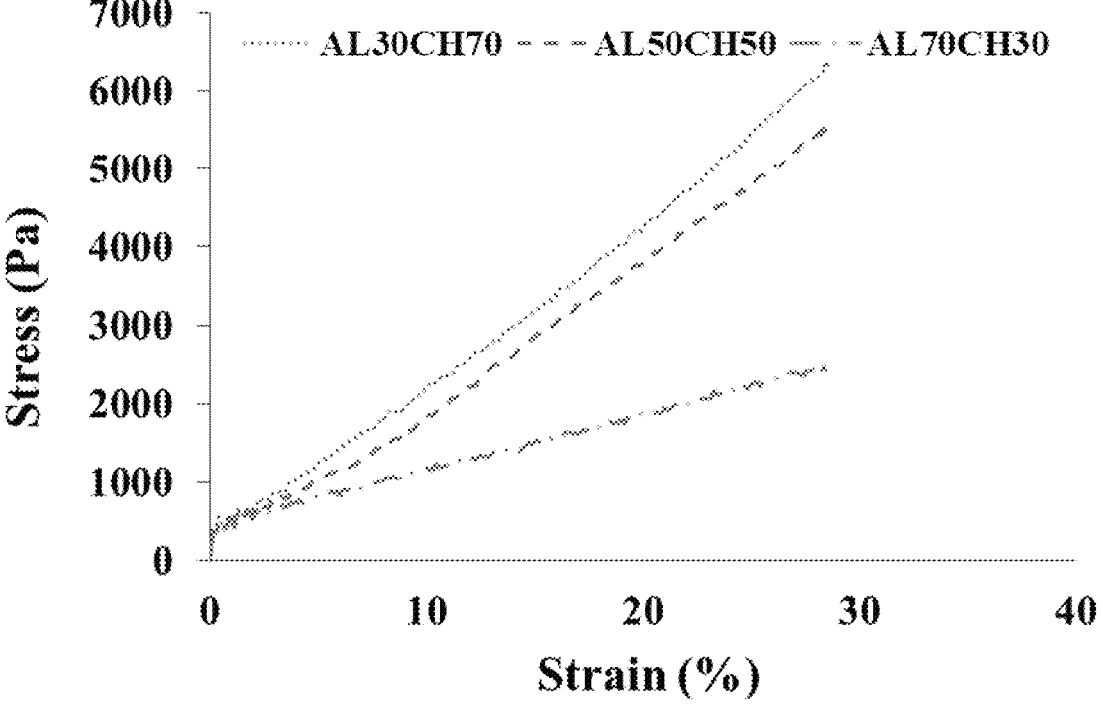
FIG. 4 depicts a graph showing stress vs strain curves for AL30CH70 (Sample 1), AL50CH50 (Sample 2) & AL70CH30 (Sample 3), with a strain rate of 2 mm/s, in accordance with an implementation of the present disclosure.

Mechanical strength was measured at 37° C. To perform the compression test, molds were prepared with a specification of 1.2 cm diameter and 0.7 cm height. The molds were filled with the samples 1, 2 and 3 (Table 2). Anti-coagulated whole blood and 0.2 M calcium chloride was then added to the samples and blood samples were allowed to clot. After that, clotted blood samples were taken out from the molds and brought for a compression test. For comparing the compressive strength of the PEC nano-fibrous samples, QuickClot™ and pure blood were used but the molds did not stand for the compression test. In the case of QuickClot™, more than 60% mass of PEC that filled the molds was required to fill the molds and clot the total blood volume, which was not the same condition for the PEC samples. Therefore, QuickClot™ could not be used. In the case of pure blood, the molds were not formed. So, the compressive mechanical strength was measured between the samples and it was found that the variation in samples of the present disclosure do not process much differences in terms of their mechanical strength. The "stress vs strain" plots for the samples is shown in FIG. 4.

Figure 5:
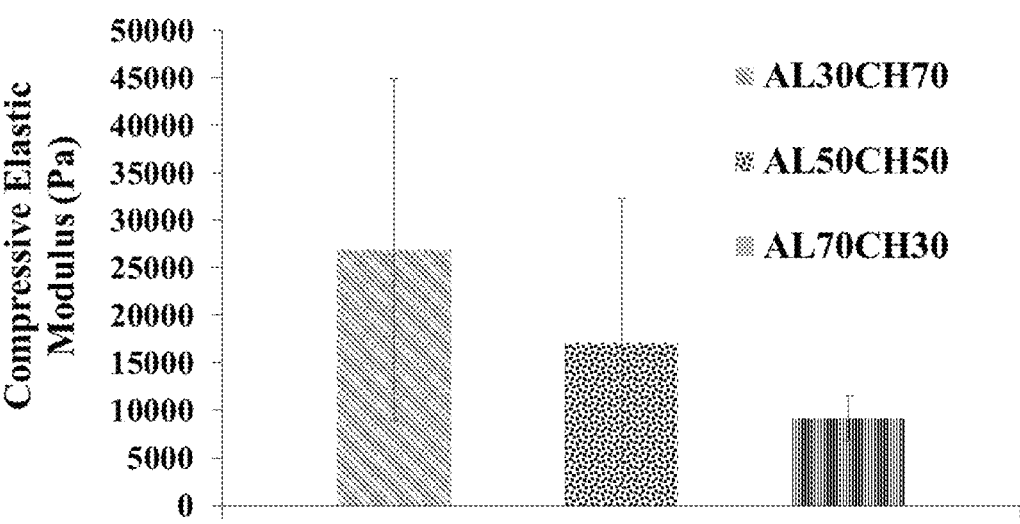
FIG. 5 depicts Compressive Elastic modulus of the blood clotted by 10% by weight of AL30CH70, AL50CH50, AL70CH30, in accordance with an implementation of the present disclosure.
Figure 6:
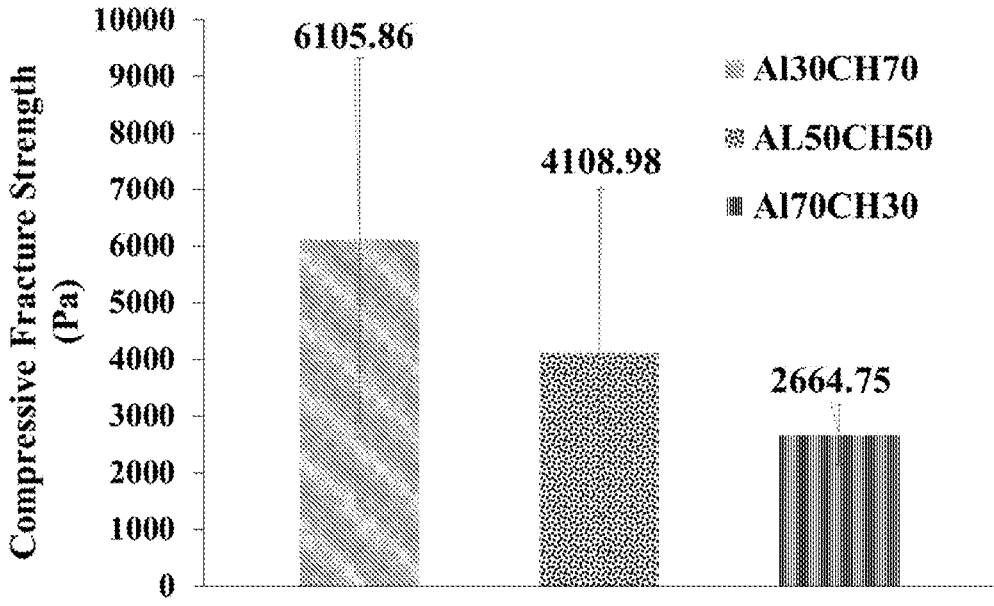
FIG. 6 depicts Compressive Fracture Strength of the blood samples clotted by 10% by weight of AL30CH70, AL50CH50, AL70CH30, in accordance with an implementation of the present disclosure.

FIGS. 5 and 6 show the compressive elastic modulus and fracture strength for the samples.

Higher chitosan containing samples showed higher elastic modulus and compressive fracture strength. It is expected since positively charged chitosan will bond strongly with negatively charged cells present in the blood.

Example 6

Surface Area Analysis

Surface area and pore size of the PEC nanofibrous powder was measured by using Brunauer-Emmett-Teller (BET) surface area analysis test. Surface area is a very important property that gives an insight into the absorption capability and area offers for the cells adhesion. The higher will be the surface area the more will be the absorption capability. Also, the more surface will get exposed to the cells for adhesion. In the case of PEC samples, because of the higher surface area, these samples have higher absorption capability because of which they start absorbing blood the moment they are applied. The measured surface area and pore size for samples are mentioned in Table 3.

TABLE 3

Surface area of AL30CH70 and AL50CH50 using BET surface area analysis.

| Sl. No. | Sample name | Surface area (without pore area)(m$^2$/g) | Surface area(with pore area) (m$^2$/g) | Pore radius (Å) |
|---|---|---|---|---|
| 1 | AL30CH70 | 81.12 ± 47.25 | 249.72 ± 110.13 | 17.63 ± 0.015 |
| 2 | AL50CH50 | 171.33 ± 80.11 | 386.19 ± 170.76 | 18.18 ± 2.22 |

AL50CH50 samples showed higher surface area compared to AL30CH70 samples. A similar trend was also observed in whole blood clotting time also. It can be concluded from this data, that higher surface area will lead to a faster clotting rate.

Example 7

Hemolysis Assay

The hemolysis test was performed to evaluate whether the PEC nano-fibrous samples are compatible with the blood cells or not. To perform this test, 0.9% NaCl solution was prepared. The anti-coagulated blood was diluted by adding the NaCl solution at 4:5 ratio (blood:NaCl solution). Equal amounts of samples were placed in a 15 ml polypropylene tubes with 6 ml of NaCl solution and kept at 37° C. for 30 minutes. After incubation, in each of the polypropylene tubes, 0.5 ml of diluted blood was added and kept at 37° C. for 2 hours. Positive and negative controls were also prepared. Positive control was made by adding 6 ml NaCl solution, 0.5 ml diluted blood and 0.01 M HCl solution. Negative control was made by adding 6 ml NaCl solution and 0.5 ml diluted blood. After 2 hours of incubation, all the samples were centrifuged at 2000 g for 20 minutes. At last OD values of the supernatants were taken at 540 nm. The test was performed in triplicate. The measured hemolysis percentage data for samples 1, 2 and 3 are mentioned in Table 4 below.

TABLE 4

| Hemocompatibility of alginate/chitosan PEC materials. | | |
|---|---|---|
| Sl. No. | Sample Name | Hemolysis (%) |
| 1 | AL30CH70 | 4.10 ± 2.6 |
| 2 | AL50CH50 | 0.94 ± 0.6 |
| 3 | AL70CH30 | 0.78 ± 0.7 |
| 4 | Celox ™ | 10.00 ± 2.8 |

All PEC samples showed lower than 5% hemolysis, which indicates that all PEC samples are blood-compatible.

Example 8

Animal Study

The present Example discusses the application of the PEC as described in the present disclosure. A total of 3 male New Zealand White rabbits weighing between 2 and 3 kgs were utilized for the study. Approximately 24 hours before the treatment, the hair on the back of both the ears was removed and the ear artery was exposed and disinfected with 70% ethanol. Rabbits were anesthetized by intramuscular injection of Ketamine hydrochloride (35 mg/kg) and xylazine (5 mg/kg). A longitudinal incision of 1.0 cm in length (wound) was made on the right ear artery.

The wound was left to bleed for 5-10 s, the blood flowing onto the surface of the ear was wiped, and then the wound was covered with test items and observed for time to haemostasis. After complete haemostasis a compression pressure was applied using 200 g weight and then observed for re-bleeding/time taken for re-bleeding. The test items AL50CH50 (Sample 2 as described in Examples 1 and 3) was applied to the right ear wound. The contralateral wound segment (left ear) was covered with gauze piece served as control. All the animals were observed for clinical signs throughout the experimental period.

Figure 7:
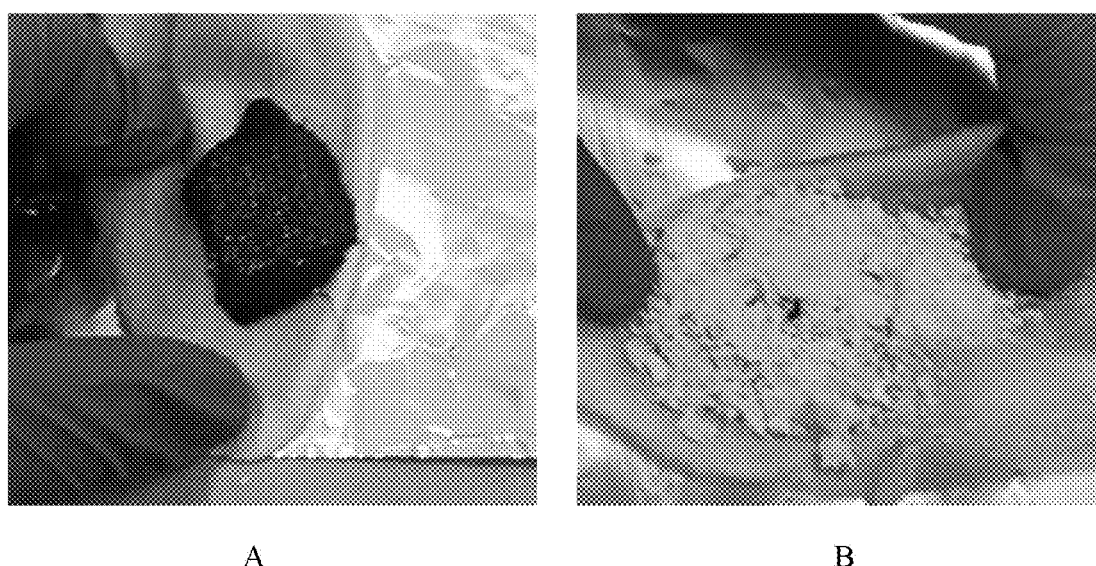
FIG. 7(A-B) depicts the animal study (rabbit) performed using the PEC as described in the present disclosure, in accordance with an implementation of the present disclosure.

There were no treatment-related clinical signs and mortalities, and no change was noticed in the body weight. The initial blood loss calculated for all three groups did not show any significant difference. The amount of test material required to complete haemostasis for AL50CH50 was 309.88±43.14 mg (Table 5). The results of time taken to complete haemostasis demonstrated in case of gauze was >120 s and by AL50CH50 was 42±4 s. There was no re-bleeding observed after 2 mins of pressure application in case of AL50CH50. FIG. 7A depicts that haemostasis was not achieved within 120 seconds in case only gauze was used. Whereas, FIG. 7B depicts that haemostasis was achieved in 42+4 in case of applying AL50CH50.

TABLE 5

| Time to complete haemostasis | | |
|---|---|---|
| | Time to Haemostasis (s) | |
| Animal No. | Test Item (AL50CH50) | Control (Gauze) |
| 1 | 47 | >120 |
| 2 | 45 | >120 |
| 3 | 33 | >120 |
| Mean ± SEM | 42 ± 4 | — |

Advantages of the Present Disclosure

The present disclosure discloses a nanofibrous polyelectrolyte complex (PEC) comprising of materials that are naturally occurring thereby minimising the chances of any side-effects that may arise while applying the PEC to the affected or wounded area. Further, because of the nanofibers present in the PEC the complex is able to achieve a rapid clotting of blood within 50 seconds of application to the affected or wounded area. The process as described herein is a very simple process to produce the PEC which is a significant advantage of the present disclosure. Also, the PEC of the present disclosure does not have an adverse effect on the blood cells as is evident by the data shown in the present disclosure.

We claim:

1. A process for preparing a polyelectrolyte complex comprising nanofibers, said process comprising: (a) obtaining a solution-I comprising at least one polycationic component having a pH in a range of 3-5 (b) obtaining a solution-II comprising at least one polyanionic component having a pH in a range of 6-8; (c) mixing the solution-I and the solution-II by adding solution-I dropwise to solution-II to obtain a mixture; and (d) processing the mixture, wherein the processing comprises (i) sonicating the mixture to obtain a sonicated sample; and (ii) washing the sonicated sample with at least one organic solvent followed by drying the sample, in order to obtain the polyelectrolyte complex, wherein the complex has a pH in a range of 3-7.

2. The process as claimed in claim 1, wherein the at least one polycationic component is selected from a group consisting of chitosan or its derivatives, poly-L-lysine, and combinations thereof.

3. The process as claimed in claim 1, wherein the at least one polyanionic component is selected from a group consisting of alginate, hyaluronic acid, dextran sulfate, carrageenan, chondroitin sulfate, pectin, polygalacturonic acid, xanthan gum, heparin, salts thereof, and combinations thereof.

4. The process as claimed in claim 1, wherein the at least one polyanionic component and the at least one polycationic component has a weight ratio in a range of 80:20 to 20:80.

5. The process as claimed in claim 1, wherein the nanofibers have a diameter in a range of 20-100 nm.

6. The process as claimed in claim 1, wherein the complex further comprises at least one compound selected from a group consisting of at least one antimicrobial agent, at least one growth factor, at least one anti-inflammatory agent, at least one anti-histamine, at least one compound containing copper or silver ions, and combinations thereof.

7. The process as claimed in claim 1, wherein the complex is hemocompatible, biodegradable and non-cytotoxic.

8. The process as claimed in claim 1, wherein the complex has a surface area (without pore area) of 33.87 to 251.44 m$^2$/g.

* * * * *